United States Patent [19]

Lamine et al.

[11] Patent Number: 5,670,717

[45] Date of Patent: Sep. 23, 1997

[54] METHOD AND DEVICE FOR DETECTING AND/OR MEASURING AT LEAST ONE GEOPHYSICAL PARAMETER FROM A CORE SAMPLE

[75] Inventors: Etienne Lamine, Court-Saint-Etienne; Patrick Honhon, Glons, both of Belgium

[73] Assignee: Baroid Technology, Inc., Houston, Tex.

[21] Appl. No.: 589,827

[22] Filed: Jan. 22, 1996

[30] Foreign Application Priority Data

May 30, 1994 [BE] Belgium ................... 09400537
May 16, 1995 [WO] WIPO ............... PCT/BE95/00048

[51] Int. Cl.$^6$ .................................................. F21B 49/02
[52] U.S. Cl. ........................ 73/152.11; 175/50; 175/244
[58] Field of Search ........................ 73/152.03, 152.11, 73/152.14, 152.43, 864.44; 175/50, 46, 58, 244, 246, 249; 250/254, 255

[56] References Cited

U.S. PATENT DOCUMENTS

| 3,025,398 | 3/1962 | Dameron ........................... 250/255 |
| 4,014,393 | 3/1977 | Hensel, Jr. ............................ 175/58 |
| 4,955,438 | 9/1990 | Juergens et al. ..................... 175/50 |
| 5,012,674 | 5/1991 | Millheim et al. ................. 73/152.03 |
| 5,206,505 | 4/1993 | Sprung ............................ 175/249 X |

FOREIGN PATENT DOCUMENTS

| 0310303-A1 | 4/1989 | European Pat. Off. . |
| PCT/BE95/00048 | 5/1995 | WIPO . |

*Primary Examiner*—Michael Brock
*Attorney, Agent, or Firm*—Browning Bushman

[57] ABSTRACT

Method and device for detecting and/or measuring at least one geophysical parameter from a core sample (1), in particular in the oil sector, comprising, during an operation of core drilling with a sampler (2); arranging, substantially fixed relative to the sampler (2), a sensor (3) for detecting and/or measuring said parameter, directly downstream of the exit orifice (5) of the sampler (2) relative to the direction of withdrawal of the core sample (1), in the vicinity of the withdrawal path of the core sample (1), detecting and/or measuring values of the parameter at at least one location on the core sample (1) while the latter is being withdrawn from and/or moved back in the sampler (2), and processing of the detected and/or measured values of the parameter, in order to store them in memory and/or use them immediately.

31 Claims, 2 Drawing Sheets

METHOD AND DEVICE FOR DETECTING AND/OR MEASURING AT LEAST ONE GEOPHYSICAL PARAMETER FROM A CORE SAMPLE

The present invention relates to a method for detecting and/or measuring at least one geophysical parameter from a core sample, in particular in the oil sector.

Geophysical parameters which are of interest to the person skilled in the art in the study of oil wells being drilled are, for example, the natural radioactivity of the core sample, the absorption of a known radiation emitted by a known source arranged in proximity to the core sample, and the value of the liquid saturation of the core sample (which value is measured by induction).

To date, this the of parameter has been measured and/or detected by arranging the core sample which has been withdrawn from the well substantially horizontally on the ground and by moving a carriage equipped with the measuring instrument or instruments manually along the core sample.

This procedure has significant disadvantages, including the fact that it is first necessary to handle the core sample. Although it is contained in an inner tube of the sampler, it is necessary, in order to transport the core sample, for example in order to lay it on the ground, to detach the successive inner tubes from one another, break the core sample at the junctions of these tubes and to cut the core sample, together with the inner tube containing it, into transportable sections of the order of approximately one meter in length, and it is necessary to close the ends of these sections. This sectioning and the operations of closure and transport affect the strata in the core sample, especially at the two ends of each section, and therefore distort the information which could be extracted from the measurements taken along the sections and mainly at their ends.

Since the carriage is moved by hand, the speed imparted to it is not uniform, and this may compromise accuracy of the measurements.

Parameters of the abovementioned type can be influenced by the environment of the core sample at the time of measurement, or else similar parameters originating from the environment may be added to the corresponding parameters of the core sample during the measurement taken therefrom. Thus, when the core sample is arranged horizontally, since one of its sides is closer to the ground than the other, this difference in distance may affect the result of the measurement, or else the ground may influence the instruments because of its proximity, this being increasingly so since this proximity is asymmetrical relative to the mass of the core sample as a whole. Overall, lack of accessibility to the core sample makes it impossible to optimize the measurement.

The object of the present invention is to overcome these problems by making it possible to detect and/or measure geodesic parameters from a core sample which has been handled as little as possible, for example because it has not yet been cut into sections, and which is situated in such a way that it is influenced by the environment as little as possible or as symmetrically as possible, because it is, for example, still held, until the time of detection and/or measurement, in the vertical position (therefore under symmetrical influence from the ground) and shielded in the outer tube of the sampler, which is made of metal and therefore forms a screen against certain influences of the surrounding ground.

In order to solve the abovementioned problems according to the invention, the process comprises, during an operation of core drilling with a sampler;

arranging, substantially fixed relative to the sampler, a sensor for detecting and/or measuring said parameter, directly downstream of the exit orifice of the sampler relative to the direction of withdrawal of the core sample, in the vicinity of the withdrawal path of the core sample, detecting and/or measuring values of the parameter at at least one location on the core sample while the latter is being withdrawn from and/or moved back in the sampler, and processing of the detected and/or measured values of the parameter, in order to store them in memory and/or use them immediately.

The present invention also relates to a device for detecting and/or measuring at least one geophysical parameter from a core sample, in particular in the oil sector.

According to the invention, the said device includes:

a hollow body having two openings situated opposite one another along a longitudinal axis of the hollow body, and a free passage extending between the two openings, the latter and the free passage being arranged so that a core sample, enclosed in an inner tube of the sampler, can pass freely from one opening to the other through the hollow body, fixing means for releasably fixing, optionally with defined play, the hollow body to an outer tube of the sampler, at the end of the latter through which a core sample enclosed in an inner tube is extracted, so that the hollow body is, at least for the most part, situated in the extension of the outer tube, the longitudinal axes of the hollow body and of the sampler being substantially coaxial, and at least one sensor for detecting and/or measuring a geophysical parameter to be evaluated from a core sample to be withdrawn from the sampler, this detection and/or measuring sensor being fixed to the hollow body in such a way that it is arranged facing the core sample enclosed in said inner tube when this core sample is in the aforementioned free passage.

Other details and particular features of the invention will emerge from the secondary claims and from the description of the drawings which are appended to the present document and which illustrate, by way of non-limiting examples, the method and one particular embodiment of the device according to the invention.

In the various figures, the same reference numerals denote identical or similar elements.

Figure 1:
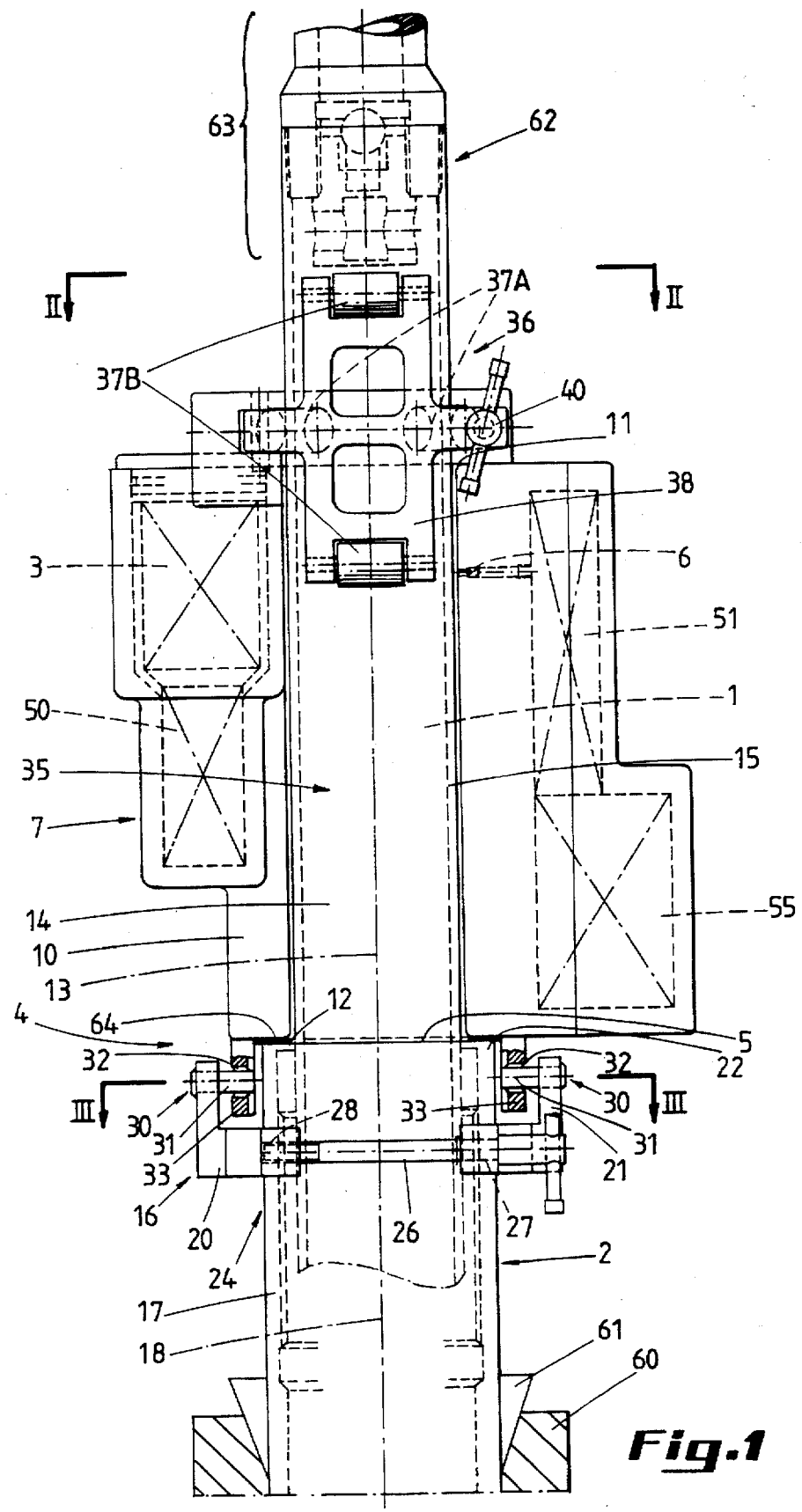
FIG. 1 shows a view in elevation and with partial cutaway of a device of the invention for implementing the method of the invention, the device being installed on a sampler and being used.

The method according to the invention is intended for detecting and/or measuring at least one geophysical parameter from a core sample 1 (FIG. 1), for example in oil industry core drilling. A geophysical parameter of this type may be natural radioactivity of the constituents of the core sample, absorption of the radiation emitted by a known radiation source, etc.

According to the invention, the method comprises, during an operation of core drilling with a sampler 2, arranging, substantially fixed relative to the sampler 2, a sensor 3 for detecting and/or measuring the parameter in question, directly downstream, at 4, of the exit orifice 5 of the sampler 2 relative to the direction of withdrawal of the core sample 1 in the immediate vicinity (known to the person skilled in the art) of the withdrawal path of the core sample 1. For example, the sensor 3 may be an NaI crystal which detects the radiation fraction, from a known cesium-137 source of 1 millicurie and situated at 6, which is not absorbed by the constituents of the core sample 1, in order to determine therefrom the radiation fraction absorbed by these constituents. The value of the parameter is therefore detected and/or measured by this sensor 3 at one or more locations on the core sample 1 while the latter is withdrawn from the sampler 2 by known means and/or is moved back therein by these means. This procedure may have the purpose, for example, of performing the same detection and/or measurement several times at a plurality of locations over the length of the core sample 1 which has just been taken and which is still only at the first handling stages, in contrast to the prior method, without therefore being cut and moved from a practically vertical position to, for example, a horizontal position before the abovementioned detection and/or measurement takes place. Preliminary processing of the values delivered by the detection and/or measurement may then also take place directly at the core drilling site, for example for the purpose of sorting these values in order to store them in memory or to use them immediately, as explained below.

Preferably, the method according to the invention further includes, simultaneously with the aforementioned detection and/or measurement at 3, acquisition of the position of the location corresponding to this detection and/or measurement on the core sample 1 and, after this acquisition, processing thereof in order to store it in memory and/or use it immediately, for example in order to determine the segments of the core sample 1 which exhibit particular detection and/or measurement results.

Advantageously, a substantially constant separation between two detection locations can be selected so as, for example, to facilitate this assignment of each detection and/or measurement location to this detection and/or measurement, or to make it possible to observe a change in the latter more easily. In addition, selection of a substantially constant speed of displacement during withdrawal of the core sample 1 from the sampler 2 or movement thereof back in the latter may be beneficial for detections and/or measurements which are influenced by this speed of displacement. Until now, this has resulted from a manual action during displacement of the aforementioned carriage and it is therefore essentially nonuniform.

Since detections and/or measurements are carried out, according to the invention, directly at the drilling site, it is preferable, for example in order to analyze them immediately, to transmit them remotely from the abovementioned site to where an operator can process them under shelter and out of the way of the workers undertaking the drilling or core sampling proper.

The invention also relates to the device mentioned above. In its simple form, this device 7 includes a hollow body 10 having two openings 11 and 12 situated opposite one another along a longitudinal axis 13 of the hollow body 10. A free passage 14 extends between the openings 11 and 12 and is arranged relative thereto so that a core sample 1, enclosed in an inner tube 15 of the sampler 2, can pass freely through the hollow body 10. The device 7 further includes fixing means 16 for releasably fixing the hollow body 10 to an outer tube 17 of the sampler 2, at the end 22 of the latter through which a core sample 1 enclosed in the inner tube 15 is extracted from the sampler 2. The hollow body 10 is then fixed therein so as to be situated, at least for the most part, in the extension of the outer tube 17, the longitudinal axes 13, of the hollow body 10, and 18 of the sampler 2, being substantially coaxial. The hollow body 10 includes at least one sensor 3 for detecting and/or measuring a geophysical parameter to be evaluated from the core sample 1 to be withdrawn from the sampler 2. The sensor 3, an example of which is given above, is fixed to the hollow body 10 in order to be arranged facing the core sample 1 when the latter is in the free passage 14.

Preferably, the aforementioned fixing means 16 may constitute an assembly that can be detached from the hollow body 10 and may comprise (FIG. 3) two clamping parts 20 and 21 matched to the external diameter of the outer tube 17 in order to be able to grip this tube 17 forcibly in the vicinity of its end 22 for extraction of the core sample 1. Linkage 23 and tightening means 24 are arranged between the two clamping parts 20 and 21. The linkage means 23 are formed, for example, by a linkage cross member 23 which joins together, in articulated fashion, one end of a clamping part 20 to a corresponding end of the other clamping part 21, so that these clamping parts 20, 21 can be moved freely, in order to grip and to release the end 22, in a plane substantially perpendicular to the longitudinal axis 18. The two clamping parts 20 and 21 can then be arranged to occupy two separate positions relative to one another, namely a first position in which (FIGS. 1 and 3) they securely grip the outer tube 17 when the device 7 is mounted thereon, and a second position (not represented) in which the clamping parts 20 and 21 are separated from one another by a distance greater than the external diameter of the outer tube 17, so as to make it possible to mount the fixing means 16 and therefore the device 7 on the outer tube 17, or to remove them therefrom.

Figure 3:
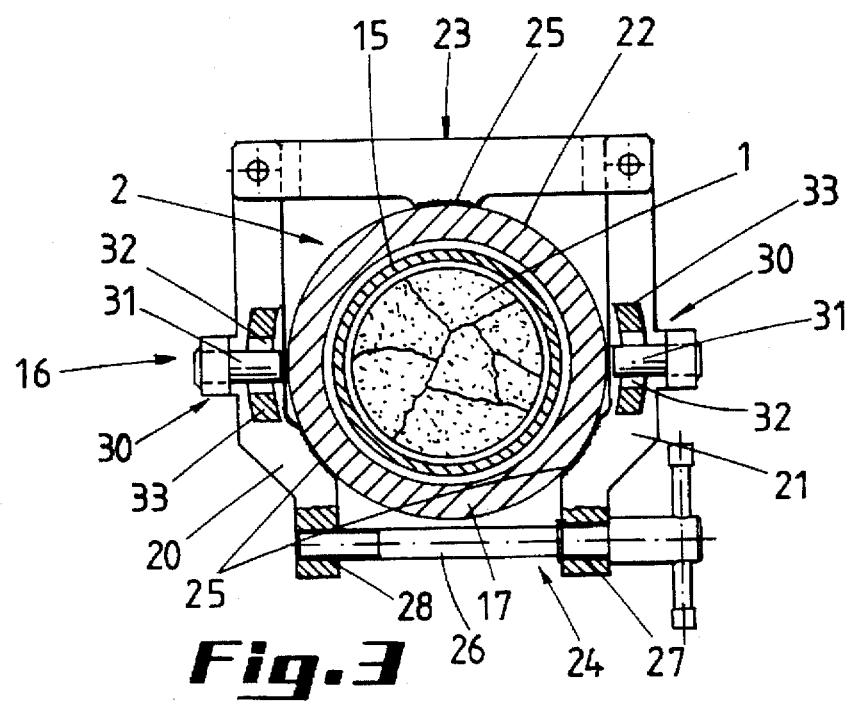
FIG. 3 is a view with cross section, on the line III—III of FIG. 1 and along the associated arrows, showing guiding of the aforementioned device relative to a sampler inner tube passed into the device.

In the example represented in FIG. 3, the clamping parts 20 and 21 and the crossmember 23 each include an internal boss 25, an internal peripheral surface of which is matched to said external diameter of the outer tube 17, the three internal bosses 25 being regularly distributed around the outer tube 17.

For the abovementioned gripping, the aforementioned tightening means 24 are, for example, a screw 26 passing through a smooth hole 27 made in the free end of the clamping part 21, and in a threaded hole 28 made in the free end of the clamping part 20. Advantageously, the screw 26, the smooth hole 27 and the threaded hole 28 have, when the linkage 23 and clamping means 24 are mounted on the outer tube 17, a common axis which is parallel to the aforementioned plane perpendicular to the longitudinal axis 18, and which extends on the opposite side of the outer tube 17 relative to the cross member 23, preferably parallel to the latter.

In order to connect the hollow body 10 proper to the linkage 23 and tightening means 24, connection means 30 are provided which may comprise projecting elements 31 and recesses 32 arranged on the hollow body 10 and, for example, on the clamping parts 20 and 21, as represented by FIG. 3. In this figure, each projection 31 is a protruding pin 31 fixed to the clamping part 20 or 21 in such a way that the two pins 31 are coaxial along a diameter of the outer tube 17, when the fixing means 16 grip the latter with the device 7 being mounted, and in such a way that the free end of each pin 31 is turned toward the longitudinal axis 18. In the aforementioned mounted state, represented in FIGS. 1 and 3, the pins 31 are passed through recesses or openings 32 made in corresponding lugs 33 of the hollow body 10, which are fixed thereto at that end of it which is to be placed on the outer tube 17. An interlock linkage is thus produced between the hollow body 10 and the linkage 23 and clamping means 24.

Preferably, play is provided between each pin 31 and the corresponding opening 32, for reasons explained below.

The aforementioned interlock linkage can be released, in the case of the above example, by unscrewing the screws 26 so that the clamping parts 20 and 21 can be moved away from one another in order to untighten their grip on the outer tube 17, until the pins 31 can be withdrawn from the openings 32.

Advantageously, in order to allow possible mounting or dismounting of the hollow body 10 on or from the sampler 2, this body has an overall U-shape in cross section at its axis 13. One longitudinal side 35 (FIGS. 1 and 2) of the hollow body 10 is actually open over its entire dimension, taken parallel to the longitudinal axis 13, and over its transverse dimension at least equal to the external diameter of the core sample 1 or, preferably, of the inner tube 15. The device 7 can thus be fitted on the core sampler 2 or withdrawn therefrom by displacement transverse to the axis 13 or 18 so that the core sample 1 or the inner tube 15 can thus, partially extracted from the sampler 2, easily enter the free passage 14 from the outside of the hollow body 10, or vice versa, when the latter is mounted on the sampler 2 or, respectively, during dismounting.

Figure 2:
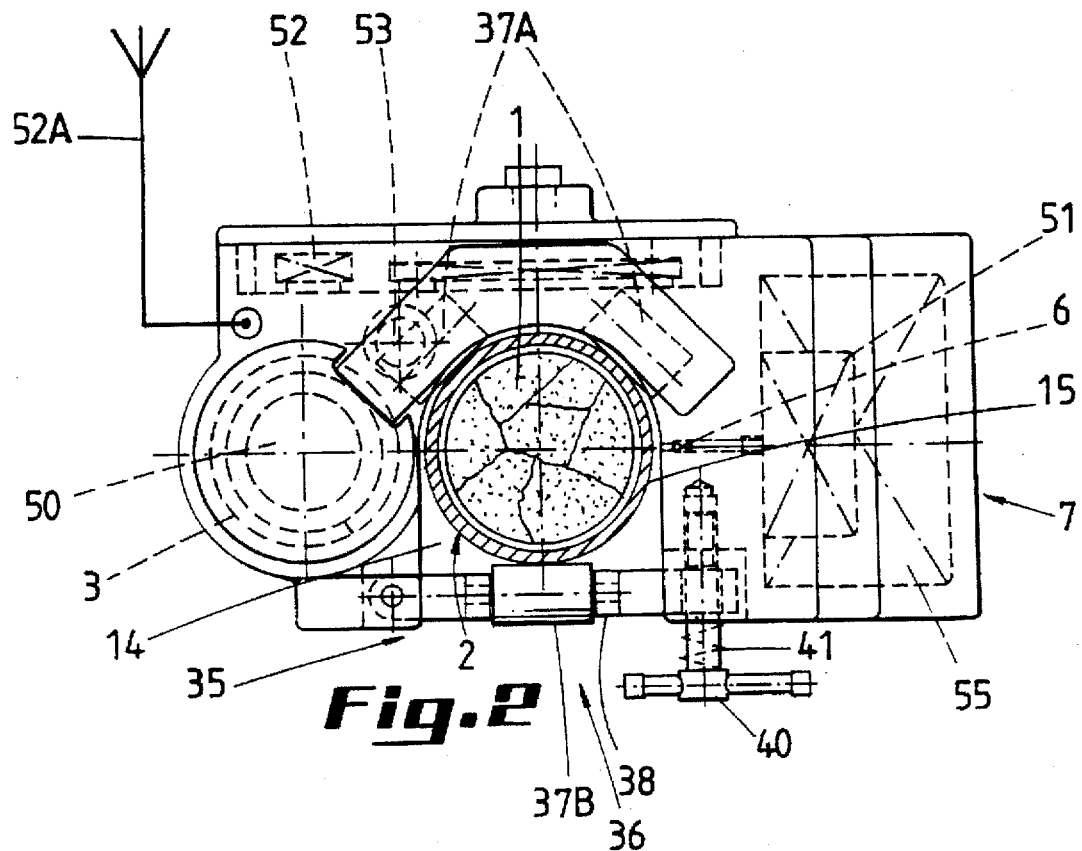
FIG. 2 is a view with cross section, on the line II—II of FIG. 1 and along the associated arrows, showing the fixing of the aforementioned device to the sampler.

In a preferred embodiment of the invention, represented in FIGS. 1 and 2, the device 7 further includes means 36 for guiding the hollow body 10 relative to the inner tube 15. These guide means 36, comprising rollers 37 whose axis of rotation is in each case in a plane perpendicular to the longitudinal axis 13, are arranged so as to bear on the external surface of the aforementioned inner tube 15 when the latter is arranged in the hollow body 10, in the measurement and/or detection position. For example, the axes of rotation of the two rollers 37A may be fixed relative to the hollow body 10 and may be situated in the same plane perpendicular to the longitudinal axis 13, preferably opposite the open longitudinal side 35 relative to the longitudinal axis 13. In the present exemplary embodiment, two other rollers 37B may be provided on a support 38 mounted on the hollow body 10 by means, on the one hand, of a hinge 39 and, on the other hand, of a screw 40 and of a compression spring 41, so as to be capable of closing or opening the longitudinal side 35 by means of this support 38 and the rollers 37B. The axes of rotation of the two rollers 37B are in planes perpendicular to the longitudinal axis 13 and situated on either side of the common perpendicular plane of the axes of the rollers 37A. The projections of the rollers 37A and 37B onto this latter plane are distributed over 360° around the projection of the inner tube 15 onto this same plane.

As shown by FIG. 1, the guide rollers 37 are situated at the end of the hollow body 10 away from the sampler 2 when the device 7 is mounted on the sampler 2.

In one embodiment of the invention, the sensor 3, formed by an NaI crystal, is connected to a photomultiplier 50 in order to detect gamma rays emitted by the core sample 1 or to measure these rays absorbed by this core sample 1.

In order to analyze the detection and/or measurement, the sensor 3 may be connected by the photomultiplier 50 to a unit 51 for processing the signals from the sensor 3, and this processing unit 51 may be connected to a transmitter 52, for example a VHF radiotransmitter, which is designed to transmit the processed signals over a distance of 50 to 100 m and which is incorporated in the device 7. The transmitter 52 is then, via its antenna 52A, tuned to a radio receiver (not represented) designed to receive the transmitted processed signals and to send them to a user. Preferably, the aforementioned transmitter 52 and receiver are each a combined transmitter/receiver and are designed so that they can, in addition, control the processing unit 51 from the receiver (not represented), via the transmitter 52.

A radioactive source 6 may be arranged in the hollow body 10 in order to radiate toward the core sample 1. The aforementioned sensor may then be designed to measure the absorption of the radiation from the source 6 by the core sample 1. A second sensor 53 may be mounted in the hollow body 10 in order to measure natural radiation originating from the core sample 1. This sensor 53 is then also connected to the processing unit 51 which, in this case, is designed to process the signals from the second sensor 53 as well and to transmit them, as above, with a view to using the away from the drilling platform which is the site of core drilling and use of the device 7.

The device 7 preferably includes its own batteries 55 for powering the aforementioned measurement, detection, processing, transmission, etc. means.

In order to use the device 7, the inner tube 17 of the sampler 2 may, for example, be blocked in the revolving table 60 (FIG. 1) of the drilling platform, by wedging blocks 61. The upper end 62 of the inner tube 15 may be grasped by known means 63, for the purpose of withdrawing this inner tube 15 and the core sample 1 from the drilled well. These grasping means 63 are, for example, suspended by a cable from a winch (which are not represented).

The hollow body 10 may be introduced transversely to the axis 18, when the support 38 is pivoted so as to free the open longitudinal side 35, and the hollow body 10 is placed on the upper end 22 of the outer tube 17 in order to be fixed thereto by the fixing means 16. A damping washer 64 (FIG. 1) may be arranged between the hollow body 10 and the aforementioned upper end 22. After this fixing has been carried out by inserting the pins 31 into the corresponding holes 32 and by tightening the screw 26, the support 38 is positioned so as to close the longitudinal side 35 and the screw 40 is tightened in order, by means of the spring 41, to press the rollers 37B in contact with the external surface of the inner tube 15 which also comes into contact with the rollers 37A.

Once the device 7 has thus been installed, the detection and/or measurement, signal processing and transmission equipment can then be engaged in order to measure and/or detect parameters, process them, optionally store them in a memory incorporated in the device 7 and/or transmit them remotely. The aforementioned winch is turned on in order to withdraw the inner tube 15 and the core sample 1 which it carries. The measurements and/or detections are carried out. If necessary, the inner tube 15 and the core sample 1 are lowered in the outer tube 17 in order to be pulled out of it again, so as to repeat the measurements and/or detections either during descent or during descent and raising, and this can be repeated as often as desired, at a desired speed that is preferably constant.

After measurement and/or detection from the core sample 1, the device 7 can be withdrawn by reversing the sequence of operations mentioned above and the core sample 1 can then be processed in a conventional manner, for other analyses that are useful in the case of the abovedescribed type of drilling.

It should be understood that the invention is in no way limited to the described embodiments, and that many changes may be made to these embodiments without departing from the scope of the present invention.

For example, an encoding wheel system for the displacement and/or distance travelled by the inner tube 15 may be used for correlating a measurement location and the corresponding measurement, it being possible for this system to be connected to the winch or to be directly in contact with the inner tube 15.

A screen may be provided in order to close the longitudinal side 35, and thereby to avoid unbalanced influencing of the core sample 1, intended for detection and/or measurement, by the device 7 and/or the environment.

We claim:

1. A method for detecting and/or measuring at least one geophysical parameter from a core sample (1), in particular in the oil sector, characterized in that it comprises, during an operation of core drilling with a sampler (2);

arranging, substantially fixed relative to the sampler (2), a sensor (3) for detecting and/or measuring said parameter, directly downstream of an exit orifice (5) of the sampler (2) relative to the direction of withdrawal of the core sample (1), in the vicinity of the withdrawal path of the core sample (1);

detecting and/or measuring values of the parameter at at least one location on the core sample (1) while the latter is being withdrawn from and/or moved back in the sampler (2); and processing of the detected and/or measured values of the parameter, in order to store them in memory and/or use them immediately.

2. The method according to claim 1, characterized in that it further comprises, simultaneously with the detection and/or measurement of the parameter, acquisition of the position of the location corresponding to this detection and/or measurement on the core sample (1) and processing of this acquisition in order to store it in memory and/or use it immediately.

3. The method according to claim 2, characterized in that it comprises selection of a constant spacing of the successive detection and/or measurement locations and/or a substantially constant speed of movement of the core sample (1) withdrawn from or moved back in the sampler (2) during the detection and/or measurement.

4. The method according to claim 2, characterized in that it further includes remote transmission of one or more of the detected and/or measured values.

5. The method according to claim 4, further including the step of remote transmission of the position of said at least one location.

6. The method according to claim 1, characterized in that it comprises selection of a constant spacing of the successive detection and/or measurement locations and/or a substantially constant speed of movement of the core sample (1) withdrawn from or moved back in the sampler (2) during the detection and/or measurement.

7. The method according to claim 6, characterized in that it further includes remote transmission of one or more of the detected and/or measured values.

8. The method according to claim 1, characterized in that it further includes remote transmission of one or more of the detected and/or measured values.

9. A device for detecting and/or measuring at least one geophysical parameter from a core sample (1), in particular in the oil sector, characterized in that it includes:

a hollow body (10) having two openings (11, 12) situated opposite one another along a longitudinal axis (13) of the hollow body (10), and a free passage (14) extending between the two openings (11, 12), the two openings (11, 12) and the free passage (14) being arranged so that a core sample (1), enclosed in an inner tube (15) of a sampler (2), can pass freely from one opening to the other (11, 12) through the hollow body (10);

fixing means (16) for releasably fixing, optionally with defined play, the hollow body (10) to an outer tube (17) of the sampler (2), at the end (22) of the latter through which a core sample (1) enclosed in an inner tube (15) is extracted, so that the hollow body (10) is, at least for the most part, situated in the extension of the outer tube (17), the longitudinal axes (13 and 18, respectively) of the hollow body (10) and of the sampler (2) being substantially coaxial; and at least one sensor (3, 53) for detecting and/or measuring a geophysical parameter to be evaluated from a core sample (1) to be withdrawn from the sampler (2), this detection and/or measuring sensor (3, 53) being fixed to the hollow body (10) in such a way that it is arranged facing the core sample (1) enclosed in said inner tube (15) when this core sample is in the aforementioned free passage (14).

10. The device according to claim 9, characterized in that the fixing means (16) form a detachable constituent assembly of the hollow body (10) and comprise:

at least two clamp parts (20, 21) matched to the external diameter of said outer tube (17) in order to be able to grip the latter securely in the vicinity of its end (22) for taking the core sample (1) out;

linkage (23) and tightening (24) means arranged between the two clamp parts (20, 21) so that the latter can occupy relative to one another two separate positions, namely a first position in which they securely grip said outer tube (17) when the device (7) is mounted on the latter, and a second position in which they are separated from one another for mounting or dismounting the device (7) on or from the outer tube (17); and detachable connection means (30) preferably comprising projecting elements (31) and recesses (32) arranged on the hollow body (10) and on the clamp parts (20, 21) in order to form an interlock linkage which, on the one hand, fixes, optionally with defined play, the hollow body (10) on the outer tube (17) when the clamp parts (20, 21) securely grip the latter when the hollow body (10) is mounted on the outer tube (17) and which, on the other hand, is released when the clamp parts (20, 21) are in their second position, separated from one another for mounting or dismounting the hollow body (10) on or from the sampler (2).

11. The device according to claim 10, characterized in that the hollow body (10) has an overall U-shape in transverse section, one longitudinal side (35) of the hollow body (10) being open over its entire dimension parallel to the axis (13) over a dimension transverse to this axis (13) at least equal to the external diameter of the core sample (1) or of the aforementioned inner tube (15), so as to make it possible to pass the core sample (1) or, respectively, the inner tube (15), transversely to the longitudinal axis (13) from the aforementioned free passage (14), through the open longitudinal side (35), out of the hollow body (10).

12. The device according to claim 11, characterized in that the sensor (3, 53) is connected to a unit (51) for processing the signals detected and/or measured by the sensor (3) and in that the processing unit (51) is connected to a radio transmitter (52) which is designed for remote transmission of said processed signals and which is mounted in said detection and/or measurement device (7), said radio transmitter (52) being tuned on a radio receiver located remotely and designed to receive said transmitted signals and to send them to a user.

13. The device according to claim 11, characterized in that it further includes a radioactive source (6), designed to radiate toward a core sample (1), and a second sensor (53) designed to measure the absorption of the radiation from the radioactive source (6) by the core sample (1).

14. The device according to claim 10, characterized in that it further includes means (36) for guiding the hollow body (10) relative to the inner tube (15), which means are fixed to the hollow body (10) and designed so as to bear on the outer surface of the abovementioned inner tube (15) arranged in the hollow body (10), the bearing taking place at at least three contact points which, seen in projection onto a plane perpendicular to the abovementioned substantially coaxial longitudinal axes (13, 18), are distributed over 360° around the inner tube (15), these bearing points being preferably in the same plane and/or on either side of this plane.

15. The device according to claim 14, characterized in that the sensor (3, 53) is connected to a unit (51) for processing the signals detected and/or measured by the sensor (3) and in that the processing unit (51) is connected to a radio transmitter (52) which is designed for remote transmission of said processed signals and which is mounted in said detection and/or measurement device (7), said radio transmitter (52) being tuned on a radio receiver located remotely and designed to receive said transmitted signals and to send them to it user.

16. The device according to claim 14, characterized in that it further includes a radioactive source (6), designed to radiate toward a core sample (1), and a second sensor (53) designed to measure the absorption of the radiation from the radioactive source (6) by the core sample (1).

17. The device according to claim 10, characterized in that the sensor (3, 53) is connected to a unit (51) for processing the signals detected and/or measured by the sensor (3) and in that the processing unit (51) is connected to a radio transmitter (52) which is designed for remote transmission of said processed signals and which is mounted in said detection and/or measurement device (7), said radio transmitter (52) being tuned on a radio receiver located remotely and designed to receive said transmitted signals and to send them to a user.

18. The device according to claim 10, characterized in that it further includes a radioactive source (6), designed to radiate toward a core sample (1), and a second sensor (53) designed to measure the absorption of the radiation from the radioactive source (6) by the core sample (1).

19. The device according to claim 9, characterized in that the hollow body (10) has an overall U-shape in transverse section, one longitudinal side (35) of the hollow body (10) being open over its entire dimension parallel to the axis (13) over a dimension transverse to this axis (13) at least equal to the external diameter of the core sample (1) or of the aforementioned inner tube (15), so as to make it possible to pass the core sample (1) or, respectively, the inner tube (15), transversely to the longitudinal axis (13) from the aforementioned free passage (14), through the open longitudinal side (35), out of the hollow body (10).

20. The device according to claim 19, characterized in that it further includes means (36) for guiding the hollow body (10) relative to the inner tube (15), which means are fixed to the hollow body (10) and designed so as to bear on the outer surface of the abovementioned inner tube (15) arranged in the hollow body (10), the bearing taking place at at least three contact points which, seen in projection onto a plane perpendicular to the abovementioned substantially coaxial longitudinal axes (13, 18), are distributed over 360° around the inner tube (15), these bearing points being preferably in the same plane and/or on either side of this plane.

21. The device according to claim 20, characterized in that it further includes a radioactive source (6), designed to radiate toward a core sample (1), and a second sensor (53) designed to measure the absorption of the radiation from the radioactive source (6) by the core sample (1).

22. The device according to claim 19, characterized in that the sensor (3, 53) is connected to a unit (51) for processing the signals detected and/or measured by the sensor (3) and in that the processing unit (51) is connected to a radio transmitter (52) which is designed for remote transmission of said processed signals and which is mounted in said detection and/or measurement device (7), said radio transmitter (52) being tuned on a radio receiver located remotely and designed to receive said transmitted signals and to send them to a user.

23. The device according to claim 19, characterized in that it further includes a radioactive source (6), designed to radiate toward a core sample (1), and a second sensor (53) designed to measure the absorption of the radiation from the radioactive source (6) by the core sample (1).

24. The device according to claim 9, characterized in that it further includes means (36) for guiding the hollow body (10) relative to the inner tube (15), which means are fixed to the hollow body (10) and designed so as to bear on the outer surface of the abovementioned inner tube (15) arranged in the hollow body (10), the bearing taking place at at least three contact points which, seen in projection onto a plane perpendicular to the abovementioned substantially coaxial longitudinal axes (13, 18), are distributed over 360° around the inner tube (15), these bearing points being preferably in the same plane and/or on either side of this plane.

25. The device according to claim 24, characterized in that the sensor (3, 53) is connected to a unit (51) for processing the signals detected and/or measured by the sensor (3) and in that the processing unit (51) is connected to a radio transmitter (52) which is designed for remote transmission of said processed signals and which is mounted in said detection and/or measurement device (7), said radio transmitter (52) being tuned on a radio receiver located remotely and designed to receive said transmitted signals and to send them to a user.

26. The device according to claim 24, characterized in that it further includes a radioactive source (6), designed to radiate toward a core sample (1), and a second sensor (53) designed to measure the absorption of the radiation from the radioactive source (6) by the core sample (1).

27. The device according to claim 9, characterized in that it further includes means (36) for guiding the hollow body (10) relative to the inner tube (15), which means are designed to bear on the outer surface of the latter which is arranged in the free passage (14) of the hollow body (10), and in that:

the hollow body includes an open longitudinal side (35);
a guide means comprises at least one roller (37B) which can rotate about an axis of rotation transverse to the longitudinal axis (13) and which is mounted removably on the hollow body (10), on the open longitudinal side (35) of the latter, in order to bear on the inner tube (15) on the same side (35) of the hollow body (10) relative to the longitudinal axis (13) and which is mounted fixed on the hollow body (10);
at least two other guide means, each comprising at least one roller (37A) which can rotate about an axis of rotation transverse to the longitudinal axis (13) and which is mounted fixed on the hollow body (10); and the axes of rotation of the three rollers (37) being arranged around the free passage (14) so that the bearing points of the three rollers (37), projected onto a plane perpendicular to the longitudinal axis (13), are substantially regularly distributed about the latter.

28. The device according to claim 9, characterized in that said at least one sensor (3, 53) includes a crystal connected to a photo-multiplier (50) in order to detect gamma rays in a core sample (1).

29. The device according to claim 9, characterized in that the sensor (3, 53) is connected to a unit (51) for processing the signals detected and/or measured by the sensor (3) and in that the processing unit (51) is connected to a radio transmitter (52) which is designed for remote transmission of said processed signals and which is mounted in said detection and/or measurement device (7), said radio transmitter (52) being tuned on a radio receiver located remotely and designed to receive said transmitted signals and to send them to a user.

30. The device according to claim 9, characterized in that it further includes a radioactive source (6), designed to radiate toward a core sample (1), and a second sensor (53) designed to measure the absorption of the radiation from the radioactive source (6) by the core sample (1).

31. A device for detecting and/or measuring at least one parameter of a core sample, comprising:

a longitudinally extending hollow body having a longitudinally extending free passage;

a fixing assembly for releasably fixing said hollow body to an outer tube of a longitudinally extending sampler, at the end of said sampler, through which a core sample enclosed in an inner tube is extracted, whereby said hollow tube is situated as an extension of said outer tube and the longitudinal axes of said hollow body and said sample are coaxial; and at least one sensor fixed to said hollow body with said sensor facing said core sample when said core sample is in said free passage of said hollow body.

* * * * *